United States Patent [19]

Eckhardt et al.

[11] Patent Number: 4,820,882
[45] Date of Patent: Apr. 11, 1989

[54] PREPARATION OF BETA-ARYL ALCOHOLS

[75] Inventors: Heinz Eckhardt, Ludwigshafen; Manfred Eggersdorfer, Frankenthal, both of Fed. Rep. of Germany

[73] Assignee: BASF Aktiengesellschaft, Ludwigshafen, Fed. Rep. of Germany

[21] Appl. No.: 144,169

[22] Filed: Jan. 15, 1988

[30] Foreign Application Priority Data

Jan. 29, 1987 [DE] Fed. Rep. of Germany ....... 3702621

[51] Int. Cl.$^4$ ................. C07C 31/135; C07C 33/22
[52] U.S. Cl. .................................................. 568/715
[58] Field of Search ............... 568/826, 867, 866, 907, 568/715

[56] References Cited

U.S. PATENT DOCUMENTS 3,532,719 10/1970 Theimer ............................ 549/385
4,162,256 7/1979 Sprecker et al. ................... 549/385

FOREIGN PATENT DOCUMENTS 433121 9/1975 U.S.S.R. .............................. 568/715

Primary Examiner—Werren B. Lone
Attorney, Agent, or Firm—Oblon, Fisher, Spivak, McClelland & Maier

[57] ABSTRACT

β-Aryl alcohols for the general forumla I

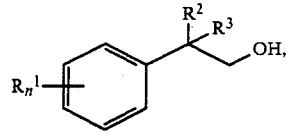

where $R^1$, $R^2$ and $R^3$ are identical or different and each is hydrogen, $C_1$-$C_{20}$-alkyl, $C_5$-$C_7$-cycloalkyl, aryl, $C_7$-$C_{12}$-aralkyl or $C_7$-$C_{12}$-alkaryl, n is 0, 1, 2, 3 or 4, or where two adjacent $R^1$'s are linked to form a 5- or 6-membered ring, are prepared by reacting an aromatic of the formula II

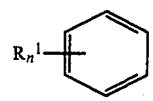

with an alkylene oxide of the formula III

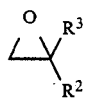

where $R^1$, $R^2$ and $R^3$ have the abovementioned meanings, in the presence of a Friedel-Crafts catalyst, by carrying out the reaction in the presence of a titanium-(IV) alcoholate at from $-20°$ to $+40°$ C. in the presence or absence of a solvent.

7 Claims, No Drawings

PREPARATION OF BETA-ARYL ALCOHOLS

The present invention relates to an improved process for preparing a β-aryl alcohol of the general formula I

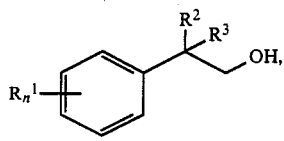

where $R^1$, $R^2$ and $R^3$ are identical or different and each is hydrogen, $C_1$–$C_{20}$-alkyl, $C_5$–$C_7$-cycloalkyl, aryl, $C_7$–$C_{12}$-aralkyl or $C_7$–$C_{12}$-alkaryl, n is 0, 1, 2, 3 or 4, or where two adjacent $R^1$'s are linked to form a 5- or 6-membered ring, by reacting an aromatic of the formula II

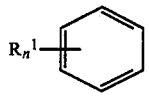

with an alkylene oxide of the formula III

where $R^1$, $R^2$ and $R^3$ have the abovementioned meanings, in the presence of a Friedel-Crafts catalyst.

The reaction of aromatic compounds with alkylene oxides in the presence of Friedel-Crafts catalysts is well known. An important reaction condition is to maintain the reaction temperature below 10° C.; in particular in the case of aromatic compounds having tertiary alkyl radicals, such as alkyl-substituted indan or 1,2,3,4-tetrahydronaphthalene, temperatures below −10° C. are required. If the solvent is a halogenated hydrocarbon, the starting materials are even reacted below −18° C. (U.S. Pat. No. 3,532,719). However, these extreme conditions are difficult to put into effect in industry, in particular since the reaction is generally highly exothermic.

There are various prior art proposals for solving this problem. In EP No. 89,207, for example, it is proposed to perform the reaction at −15° C. under reduced pressure, so that the solvent is at the boil and this way removes the heat of reaction. However, to condense the solvent it is necessary to cool to very low temperatures with dry ice to minimize solvent loss; the process is therefore very expensive. In U.S. Pat. No. 4,162,256, an increase in the reaction temperature from −20° to −5° C. is achieved by adding an aliphatic hydrocarbon as solvent. The examples given here clearly show the temperature dependence of the reaction. At −10° C. the yield, based on propylene oxide, is 42–44% (Examples 1, 2 and 4), but at −5° C. only 27% (Example 3). The conversion obtained for starting material I is very low and requires a high recycling rate. For this reason even this does not provide a satisfactory solution to the problematics of performing the reaction.

It is an object of the present invention to carry out the Friedel-Crafts alkylation described without incurring the abovementioned disadvantages.

We have found that this object is achieved with a process for preparing a β-aryl alcohol of the general formula I defined at the beginning by reacting an aromatic of the formula II

with an alkylene oxide of the formula III

in the presence of a Friedel-Crafts catalyst, which comprises carrying out the reaction in the presence of a titanium(IV) alcoholate at from −20° C. to +40° C. in the presence or absence of a solvent.

The titanium(IV) alcoholate to be used according to the invention, which is also referred to as a titanic ester or orthotitanate, is a compound of the general formula IV

where $R^4$ is an inert organic radical, for example alkyl, cycloalkyl, aralkyl or aryl. Alkyl is for example branched or unbranched $C_1$–$C_{12}$-alkyl, in particular $C_1$–$C_8$-alkyl, eg. methyl, ethyl, propyl, isopropyl, butyl, isobutyl, pentyl, hexyl or dodecyl. Cycloalkyl is for example cyclopentyl or cyclohexyl, and aryl and aralkyl are for example phenyl and benzyl. Because they are readily available, tetraalkyl titanates, in particular those where $R^4$ is $C_1$–$C_6$-alkyl, are particularly preferred.

Specific examples of titanates are: tetramethyl titanate, tetraethyl titanate, tetrapropyl titanate, tetraisopropyl titanate and tetrabutyl titanate.

Even small amounts of titanium(IV) alcoholate lead to a substantial improvement in the process. For instance, it is advantageously possible to use amounts from 0.002 to 0.1, in particular from 0.005 to 0.05, mole per mole of starting material II. Larger amounts are possible, but in general do not produce any further advantages.

The reaction can be carried out in the absence or advantageously in the presence of solvents or diluents, in which case the solvents customary in Friedel-Crafts reactions can be used. Particularly advantageously, the solvents used can be halogenated aliphatic and aromatic hydrocarbons and/or excess starting material II. The solvents can be used in the pure form or as mixtures.

Examples of aliphatic and cycloaliphatic hydrocarbons are pentane, hexane, petroleum ether, cyclohexane, 2,2,4-trimethylpentane and octane. Examples of halogenated aliphatic hydrocarbons are halogenated alkanes, alkenes or cycloalkanes such as dichloromethane, chloroform, tetrachloromethane, 1,2-dichloroethane, 1,1-dichloroethane, 1,1,2-trichloroethane, 1,1,2,2-tetrachloroethane, 1,2-dichloropropane, 1,3-dichloropropane, 1,1,2-trichloro-1,2,2-trifluoroethane, trichloroethene and tetrachloroethene. Aromatic halohydrocarbons are for example chlorobenzene and dichlorobenzene.

The reaction temperature can range from −20° to 40° C. The most suitable temperature depends on the starting materials II and III used and on the solvent and needs to be determined for each specific case. More particularly, if hydrocarbons and/or excess starting material II are used as solvent, temperatures from −10° C. to +40° C., in particular from 0° to 30° C., are advantageous. The corresponding temperature range if halohydrocarbons are used is advantageously from −20° to +20° C., in particular from −10° to +15° C. The reactions can also be carried out at the hitherto customary low temperatures, but in this case the addition of titanium(IV) alcoholate then does not produce any significant benefits.

The Friedel-Crafts catalyst can be any conventional compound in particular titanium tetrachloride and particularly preferably aluminum chloride, amounts from 0.5 to 4, preferably from 0.8 to 1.5, moles of catalyst per mole of starting material II being advantageous.

In the starting material II, $R^1$ can be hydrogen, $C_1$–$C_{20}$-cycloalkyl, in particular $C_1$–$C_8$-cycloalkyl, preferably $C_5$–$C_6$-cycloalkyl, aryl such as phenyl or $C_7$–$C_{12}$-aralkyl or $C_7$–$C_{12}$-alkenyl, for example phenylalkyl such as benzyl or phenylethyl, or tolyl. If n is greater than 1, the $R^1$'s can be identical or different. The radicals mentioned may also carry substituents which are inert under the reaction conditions, such as $C_1$–$C_4$-alkyl, or aromatically bonded halogen. Specific examples of $R^1$ are: methyl, ethyl, propyl, isopropyl, butyl, isobutyl, tert-butyl, cyclopentyl, cyclohexyl, phenyl, tolyl, benzyl and phenylethyl.

Two adjacent $R^1$'s can also be bonded to each other to form a 5- or 6-membered ring which may carry substituents, in particular $C_1$–$C_4$-alkyl, eg. methyl.

Preferred starting materials II are: benzene, toluene, o-, p- or m-xylene, ethylbenzene, isopropylbenzene, tert-butylbenzene, indan or 1,2,3,4-tetrahydronaphthalene (Tetralin ®) and their alkyl-substituted derivatives such as 1,1,2,3,3-pentamethylindan, 1-ethyl-1,3,3-trimethylindan or 1,1,4,4-tetramethyl-1,2,3,4-tetrahydro-naphthalene.

In the alkylene oxides III, $R^2$ and $R^3$ can be defined in the same way as $R^1$, ie. as hydrogen, $C_1$–$C_{20}$-alkyl, $C_5$–$C_8$-cycloalkyl, aryl, $C_7$–$C_{12}$-aralkyl or $C_7$–$C_{12}$-alkaryl. Preference is given to alkylene oxides where $R^2$ and $R^3$ are each hydrogen or a low molecular weight alkyl of 1 to 8, in particular 1 to 4, carbon atoms. Suitable compounds are for example: ethylene oxide, 1-methylethylene oxide, 1,1-dimethylethylene oxide, dimethylethylene oxide, 1-ethylethylene oxide, 1-propylethylene oxide, 1-isopropylethylene oxide, 1-butylethylene oxide, 1-sec-butylethylene oxide, 1-tert-butylethylene oxide, 1-pentylethylene oxide and 1-hexylethylene oxide. Particularly preferred starting materials III are ethylene oxide, propylene oxide, butylene 1,2-oxide and 1,1-dimethylethylene oxide.

Per mole of starting material II it is advantageous to use from 0.5 to 4, preferably from 1 to 2, moles of alkylene oxide III. The reaction can advantageously be carried out in the presence of from 0.1 to 3, preferably from 0.3 to 2, liters of solvent per mole of II.

The reaction can advantageously be performed by introducing initially into a stirred vessel the starting material II with the titanium alcoholate IV and the aluminum chloride together with a portion of the solvent. A mixture of solvent and alkylene oxide III is metered in at the desired reaction temperature in the course of from 1 to 10 hours, the amount of solvent in the add solution being preferably dimensioned in such as way that the concentration of alkylene oxide III is not more than 60%. However, it is also possible to introduce initially the entire amount of solvent. The add solution can be metered in not only above but also below the surface of the liquid; in the latter case it is advantageous to pass a stream of nitrogen through the solution at the same time. After the reaction has ended, the reaction mixture can be worked up in a conventional manner, for example by adding water, separating the phases and distillation.

Using the process according to the invention it is surprisingly possible to carry out the reaction of aromatic compounds II with alkylene oxides III in the presence of Friedel-Crafts catalysts such as $AlCl_3$ with good results at higher temperatures than in the prior art.

The solvents used can preferably also be those halogenated hydrocarbons of which it was known that preferably low temperatures had to be chosen to obtain good yields and high conversions. A further advantage of the process according to the invention is that the reaction can be carried out in conventional reaction vessels and in particular that no special cooling equipment is necessary. As a consequence of the higher reaction temperature, the reaction proceeds at a higher rate, the heat of reaction is easier to remove, on account of the lower viscosity, and the reaction time can be kept to a minimum, so that decomposition reactions and the formation of high-boiling byproducts are prevented.

The β-aryl alcoholates advantageously preparable by the process according to the invention are either used direct as scents, as is the case with phenylethanol and tolylethanol, or are used as intermediates for preparing scents, eg. 2'-(1,1,2,3,3-pentamethylindan-5-yl)propanol, and for preparing crop protection agents and drugs.

EXAMPLES 1 TO 3

Preparation of 2'-(1,1,2,3,3-pentamethylinda-5-yl)propanol in dichloromethane

At −10° C., 63 g (0.3 mol) of 1,1,2,3,3-pentamethylindan were introduced initially together with 44 g (0.33 mol) of $AlCl_3$ and an amount of titanium tetrabutylate as specified in Table 1, in 50 ml of dichloromethane. 19.3 g (0.33 mol) of propylene oxide, dissolved in 50 ml of the solvent, were added at the temperature stated in Table 1 in the course of 1 h while stirring and passing in nitrogen. After the reaction mixture was hydrolyzed, the yield was determined by gas chromatography.

TABLE 1

| Example | Ti(OC$_4$H$_9$)$_4$ | | Temperature °C. | Yield % | |
|---|---|---|---|---|---|
| | g | mol | | (a) | (b) |
| 1 | 6 | 1.76 × 10$^{-2}$ | 0 | 37 | 92 |
| 2 | 6 | 1.76 × 10$^{-2}$ | +10 | 29 | 92 |
| 2a | — | — | +10 | 20 | 43 |
| 3 | 3 | 0.88 × 10$^{-2}$ | −10 | 35 | 95 |

(a) based on propylene oxide
(b) based on converted pentamethylindan

EXAMPLES 4 TO 15

Preparation of 2'-(1,1,2,3,3-pentamethylindan-5-yl)propanol in various solvents

Example 1 is repeated, except that only 1.5 g (0.44×10⁻² mol) of titanium tetrabutylate were used and the dichloromethane was replaced by the solvent indicated in Table 2. The reaction temperature ranged from −5° to 0° C.

TABLE 2

| Example | Solvent | Yield (a) | Yield (b) |
| --- | --- | --- | --- |
| 4 | Chlorobenzene | 38% | 93% |
| 5 | Trichloroethene | 32% | 95% |
| 6 | 1,2-Dichloroethane | 34% | 80% |
| 7 | Tetrachloroethene | 25% | 89% |
| 8 | 1,1,2-Trichloroethane | 46% | 90% |
| 9 | 1,2-Dichloropropane | 26% | 90% |
| 10 | 1,1,2-Trichloro-1,2,2-trifluoroethane | 22% | 91% |
| 11 | o-Dichlorobenzene | 45% | 96% |
| 12 | 1,1,2,2-Tetrachloroethane | 41% | 96% |
| 13 | 1,2-Dichloroethane | 32% | 91% |
| 14 | 50% 1,2-Dichloroethane 50% Tetrachloroethene | 39% | 92% |
| 15 | 50% 1,2-Dichloropropane 50% Tetrachloroethene | 44% | 91% |

(a) based on propylene oxide
(b) based on converted pentamethylindan

EXAMPLE 16

At −10° C., 100 g (0.5 mol) of 1,1,2,3,3-pentamethylindan were introduced initially together with 88 g (0.66 mol) of AlCl₃ and 3 g (0.88×10⁻² mol) of titanium tetrabutylate in 100 ml of dichloromethane. 38.6 g (0.66 mol) of propylene oxide, dissolved in 100 ml of dichloromethane, were added at from −5° C. to 0° C. in the course of 8 h while stirring and passing in nitrogen. Distillation gives 46 g of unconverted 1,1,2,3,3-pentamethylindan (54% conversion) and 64.4 g of 2'-(1,1,2,3,3-pentamethylindan-5-yl)propanol having a boiling point of 140°-145° C./1 mbar, corresponding to a yield of 91%, based on converted 1,1,2,3,3-pentamethylindan.

EXAMPLE 17

At −10° C., 94 g (0.50 mol) of 1,1,2,3,3-pentamethylindan were introduced initially together with 80 g (0.6 mol) of AlCl₃ in 100 ml of tetrachloroethene and 100 ml of 1,2-dichloropropane and 2.5 g (0.73×10⁻² mol) of titanium tetrabutylate. 35 g (0.6 mol) of propylene oxide, dissolved in 100 ml of tetrachloroethene and 100 ml of 1,2-dichloropropane, were added at from −5° C. to 0° C. in the course of 2 h while stirring and passing in nitrogen. Distillation gives 31 g of 1,1,2,3,3-pentamethylindan (67% conversion) and 71 g of 2'-(1,1,2,3,3-pentamethylindan-5-yl)propanol, corresponding to a yield of 86%, based on converted 1,1,2,3,3-pentamethylindan and 48% based on starting propylene oxide.

EXAMPLE 18

Preparation of 2'-(1,1,2,3,3-pentamethylindan-5-yl)propanol in the presence or absence of titanium tetraisopropylate A 250 ml stirred vessel was charged with 44 g (0.33 mol) of AlCl₃, 63 g (0.3 mol) of 1,1,2,3,3-pentamethylindan and 50 ml of cyclohexane. A mixture of 19.3 g (0.33 mol) of propylene oxide and 50 ml of cyclohexane was added at 25°-30° C. in the course of 1 h while stirring and passing in nitrogen. A total reaction time of 2 h was followed by hydrolysis and determination of the yield by gas chromatography. The conversion of 1,1,2,3,3-pentamethylindan was 50%, and the yield of 2'-(1,1,2,3,3-pentamethylindan-5-yl)propanol, based on converted 1,1,2,3,3-pentamethylindan, 5%. Chiefly higher-boiling byproducts were obtained. If, on the other hand, the reaction is carried out in the presence of 25 g (8.8×10⁻² mol) of titanium tetraisopropylate, the yield, based on converted 1,1,2,3,3-pentamethylindan, rises to 80%.

EXAMPLES 19 AND 20

Preparation of 2-tolylethanol 400 g of dichloroethane and 110 g (1.2 mol) of toluene were introduced initially together with 63 g (0.47 mol) of AlCl₃ in the presence of 3 g (10⁻² mol) of titanium tetraisopropylate or in the absence of titanium alcoholate. 44 g (1 mol) of ethylene oxide were added in the course of 1.5 h at the temperature stated in Table 3. After hydrolysis the reaction mixture was concentrated and analyzed by gas chromatography. The yields of 2-tolylethanol, obtained as a mixture of isomers, based on converted toluene, are shown in the following table:

TABLE 3

| Example | Ti(i-C₃H₇)₄ mol | Temperature °C. | Yield % |
| --- | --- | --- | --- |
| 19 | 0.01 | 0 | 96 |
| 19a | — | 0 | 89 |
| 20 | 0.01 | +10 | 56 |
| 20a | — | +10 | 42 |

We claim:

1. A process for preparing a β-aryl alcohol of the general formula I

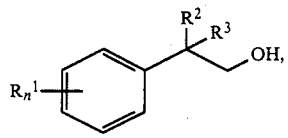

where R¹, R² and R³ are identical or different and each is hydrogen, C₁-C₂₀-alkyl, C₅-C₇-cycloalkyl, aryl, C₇-C₁₂-aralkyl or C₇-C₁₂-alkaryl, n is 0, 1, 2, 3 or 4, or where two adjacent R¹'s are linked to form a 5- or 6-membered ring, by reacting an aromatic of the formula II

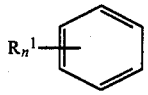

with an alkylene oxide of the formula III

where R¹, R² and R³ have the abovementioned meanings, in the presence of a Friedel-Crafts catalyst, which comprises carrying out the reaction in the presence of a titanium(IV) alcoholate at from −20° to +40° C. in the presence or absence of a solvent.

2. A process as claimed in claim 1, wherein a titanium(IV) alcoholate of the formula IV $$Ti(OR^4)_4 \qquad \qquad IV,$$

where $R^4$ is $C_1$–$C_6$-alkyl, is used.

3. A process as claimed in claim 1, wherein from 0.002 to 0.1 mole of titanium(IV) alcoholate is used per mole of starting material II.

4. A process as claimed in claim 1, wherein the reaction is carried out in a halogenated hydrocarbon as solvent at from −20° to +20° C.

5. A process as claimed in claim 1, wherein the reaction is carried out in a hydrocarbon or in the presence of excess starting material II as solvent at from −10° to +40° C.

6. A process as claimed in claim 1, wherein the Friedel-Crafts catalyst used is aluminum chloride.

7. A process as claimed in claim 1, wherein the aromatic II used is indan, 1,2,3,4-tetrahydronaphthalene or an alkylsubstituted derivative thereof.

* * * * *